US00PP22004P2

(12) United States Plant Patent
Brand

(10) Patent No.: US PP22,004 P2
(45) Date of Patent: Jul. 5, 2011

(54) ***ANDROMEDA* PLANT NAMED 'BLUE LAGOON'**

(50) Latin Name: *Andromeda polifolia*
Varietal Denomination: Blue Lagoon

(76) Inventor: Marcel Brand, Boskoop (NL)

( * ) Notice: Subject to any disclaimer, the term of this patent is extended or adjusted under 35 U.S.C. 154(b) by 0 days.

(21) Appl. No.: 12/800,262

(22) Filed: May 12, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Upov Plant Variety Database 2011/01 p. 1.*

* cited by examiner

*Primary Examiner* — Annette Para
(74) *Attorney, Agent, or Firm* — Penny J. Aguirre

(57) ABSTRACT

A new cultivar of *Andromeda* named 'Blue Lagoon', characterized by its grayish blue foliage, its freely branched habit, its pink flowers in spring, and its hardiness at least to U.S.D.A. Zone 5.

2 Drawing Sheets

Botanical classification: *Andromeda polifolia.*
Cultivar designation: 'Blue Lagoon'.

BACKGROUND OF THE INVENTION

The present invention relates to a new and distinct cultivar of *Andromeda polifolia* known as *Andromeda* 'Blue Lagoon' and will be referred to hereafter by its cultivar name, 'Blue Lagoon'.

The inventor discovered 'Blue Lagoon' as a naturally occurring branch mutation of *Andromeda polifolia* 'Blue Ice' (not patented) in March 2006 in the Inventor's nursery in Boskoop, the Netherland.

Asexual reproduction of the new cultivar was first accomplished by the Inventor using semi-ripe stem cuttings in Boskoop, the Netherland in March 2006. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Blue Lagoon' as a new and distinct cultivar of *Andromeda.*

1. 'Blue Lagoon' exhibits grayish blue leaf coloration.
2. 'Blue Lagoon' is freely branched.
3. 'Blue Lagoon' exhibits pink flowers between March and April in Europe.
4. 'Blue Lagoon' exhibits hardiness at least to U.S.D.A. Zone 5.

'Blue Lagoon' differs from its female parent, 'Blue Ice', in leaf coloration. 'Blue Lagoon' has grayish blue leaves, whereas 'Blue Ice' has greenish grey leaves. Plants of the species, *Andromeda polifolia*, exhibit green foliage. There are no other cultivars that are similar to 'Blue Lagoon' that are known to The Inventor.

BRIEF DESCRIPTION OF THE DRAWING

The accompanying colored photographs illustrate the overall appearance and distinct characteristics of the new

*Andromeda*. The photographs were taken of a 3 year-old plant as grown outdoors in a 3-liter container in Boskoop, the Netherlands.

Figure 1:
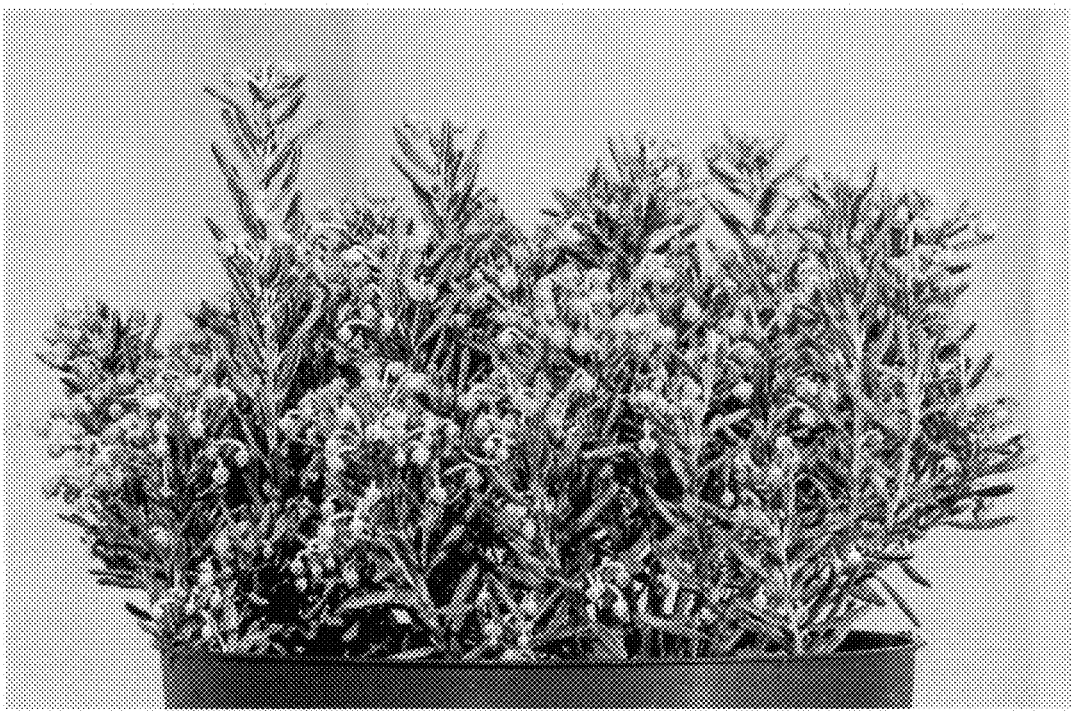
Figure 2:
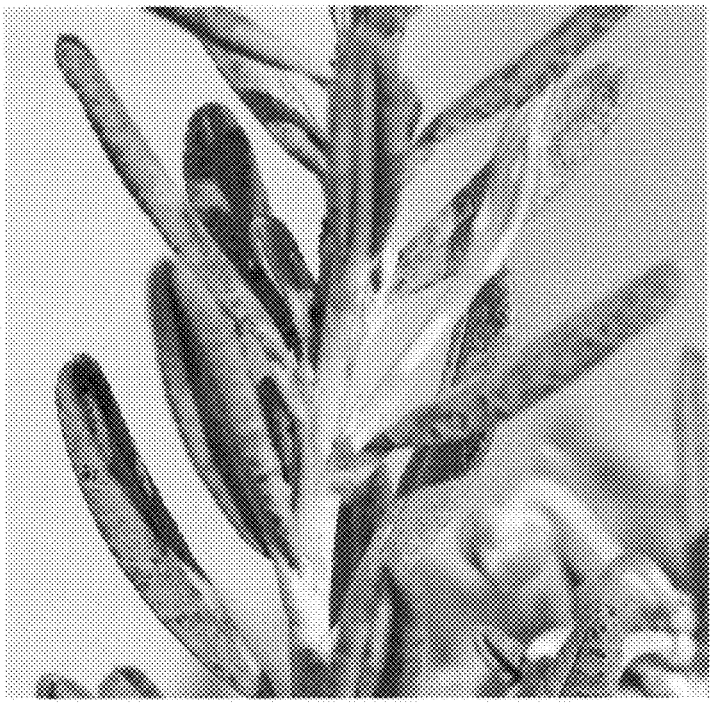
Figure 3:
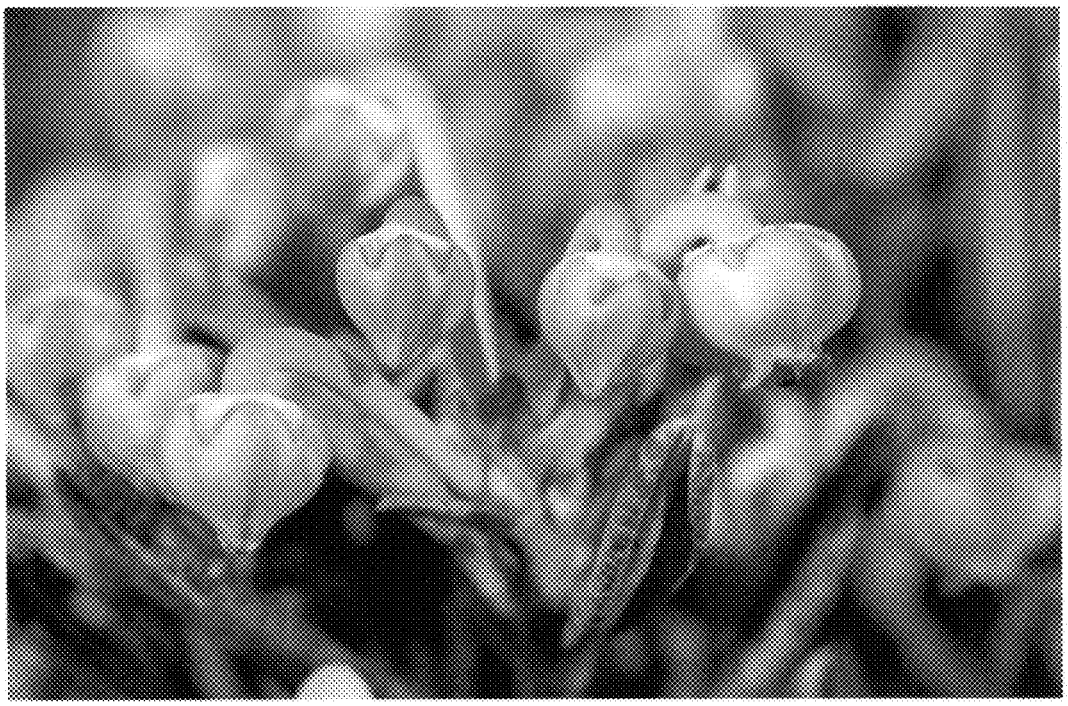

The photograph in FIG. 1 provides a view of the habit of 'Blue Lagoon' in bloom, the photograph in FIG. 2 provides a close-up view of the foliage of 'Blue Lagoon', and the photograph in FIG. 3 provides a close-up view of the flowers of 'Blue Lagoon'. The colors in the photographs are as close as possible with the digital photography techniques available, the color values cited in the detailed botanical description accurately describe the colors of the new *Andromeda.*

DETAILED BOTANICAL DESCRIPTION OF THE PLANT

The following is a detailed description of plants of the new cultivar as grown in 2-liter containers outdoors in Boskoop, the Netherlands. Plants were grown under average day temperatures of −1° to 7° C. and average night temperatures of −8° to −1° C. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General plant characteristics:

*Plant type.*—Perennial evergreen shrub.

*Plant habit.*—Broad-upright, mounded, globular in shape.

*Flowering period.*—From March to May in Europe.

*Height and spread.*—Reaches about 21.8 cm in height and 23.3 cm in width (2 year-old plant).

*Cold hardiness.*—At least to U.S.D.A. Zone 5.

*Diseases and pests.*—No greater susceptibility or resistance to disease or pest than other *Andromeda* cultivars.

*Root description.*—Fibrous.

Growth and propagation:

*Propagation.*—Semi-ripe cuttings.

*Growth rate.*—Low to moderate, young field grown plants grow approximately 7 cm per season.

*Crop time.*—Approximately 2 years from a cutting to finish in 2-liter container.

Stem description:

*Stem size.*—Lateral branches are 16.4 cm in length and 2 mm in width.

*Stem shape.*—Round.

*Stem color.*—192C to 192D becoming N199c to N199D when mature.

*Stem surface.*—Glabrous, smooth, dull.

*Stem strength.*—Very strong.

*Internode length.*—5 mm.

*Branching habit.*—Freely branched, average 66 lateral branches per plant.

*Branching aspect.*—Upright with basal branching.

Foliage description:

*Leaf shape.*—Narrow elliptic, moderately convex, midrib furrowed.

*Leaf division.*—Simple.

*Leaf base.*—Rounded.

*Leaf apex.*—Abruptly acute.

*Leaf venation.*—Pinnate, N189A covered by thin waxy layer 122C in color on upper surface and 144C on lower surface.

*Leaf margins.*—Entire, strongly revolute.

*Leaf attachment.*—Petiolate.

*Petiole.*—Average of 3 mm in length and 0.75 mm in width, 144C to 144D in color covered by thin waxy layer 122C in color.

*Leaf arrangement.*—Alternate.

*Leaf surface.*—Glabrous, smooth, dull.

*Leaf color.*—Upper surface young foliage; 189A, covered with thick waxy layer 122C, lower surface young foliage; 188C to 188D, upper surface mature foliage; N189A and covered with thin waxy layer 122C, lower surface mature foliage; 188C to 188D.

*Leaf number.*—Average of 32 per lateral branch.

*Leaf size.*—Average of 2.1 cm in length and 4 mm in width.

*Leaf aspect.*—Upright, held at about 45° angle to lateral branch.

*Leaf fragrance.*—None.

*Leaf durability to stresses.*—High.

Inflorescence description:

*Inflorescence.*—Terminal umbelliform racemes, average of 1.4 cm in length and 2.4 cm in width, 7 flowers per inflorescence, approximately 1500 flowers and buds per plant.

*Flowers.*—Urceolate, single.

*Flower bud.*—Urceolate, reflexed, an average of 4 mm in length and 4 mm in diameter, 70C in color with diffuse striations of 76D and 63B.

*Flowering habit.*—Lastingness 14 days, self-cleaning.

*Sepals.*—5, Rotate in arrangement, ovate in shape, apex acute, margin entire, base broadly acute, about 2.5 mm in length and 1.5 mm in width, upper surface 60B to 60C in color with base 76C to 76D, lower surface 60B to 60C in color.

*Petals.*—5, ovate in shape, fused throughout except at apex, surface smooth and dull, apex acute, apical margin entire, about 4.5 mm in length and 3.5 mm in width, 75B to 75C in color.

*Pedicels.*—Round, fragile, about 1.1 cm in length and 1 mm in diameter, emerging between a 0° to 30° angle from main stem, 70B in color and 69C to 69D towards base.

*Androecium.*—10 stamens, about 2 mm in length, anthers; dorsifixed, reniform with mucronate apex, 1 mm in length, 200A in color, filament; 1 mm in length, 75D in color, pollen; moderate in abundance, 155A in color.

*Gynoecium.*—1 pistil, 2.5 mm in length, stigma; club-shaped, 200A to 200B in color, 2 mm in length, style; 2 mm in length, 196A to 196B in color, ovary; inferior, 147A to 147B in color.

*Fruits/seeds.*—No fruits or seeds observed to date.

It is claimed:

1. A new and distinct cultivar of *Andromeda* plant named 'Blue Lagoon' as herein illustrated and described.

* * * * *